US007781455B2

(12) United States Patent
Arányi et al.

(10) Patent No.: US 7,781,455 B2
(45) Date of Patent: Aug. 24, 2010

(54) COMPOUNDS

(75) Inventors: Péter Arányi, Budapest (HU); László Balázs, Dunakeszi (HU); Imre Bata, Budapest (HU); Sándor Bátori, Budapest (HU); Éva Boronkay, Budapest (HU); Zoltán Kapui, Etele (HU); Edit Susán, Dunakeszi (HU); Tibor Szabó, Budapest (HU); Lajos T. Nagy, Budapest (HU); Katalin Urbán-Szabó, Budapest (HU); Márton Varga, Dunakeszi (HU)

(73) Assignee: sanofi-aventis, Paris (FR)

( * ) Notice: Subject to any disclaimer, the term of this patent is extended or adjusted under 35 U.S.C. 154(b) by 1173 days.

(21) Appl. No.: 10/518,114

(22) PCT Filed: Jun. 11, 2003

(86) PCT No.: PCT/HU03/00041

§ 371 (c)(1),
(2), (4) Date: Mar. 21, 2005

(87) PCT Pub. No.: WO03/074500

PCT Pub. Date: Sep. 12, 2003

(65) Prior Publication Data

US 2005/0153973 A1 Jul. 14, 2005

(30) Foreign Application Priority Data

Jun. 14, 2002 (HU) .................................. 0202001

(51) Int. Cl.
*A61K 31/44* (2006.01)
*A01N 43/42* (2006.01)
*C07D 417/00* (2006.01)
*C07D 401/00* (2006.01)
*C07D 413/00* (2006.01)

(52) U.S. Cl. ..................................... 514/304; 546/125
(58) Field of Classification Search ................ 546/193, 546/196, 112, 125; 514/299, 318
See application file for complete search history.

(56) References Cited

U.S. PATENT DOCUMENTS 4,273,778 A 6/1981 Hadley et al.

FOREIGN PATENT DOCUMENTS

| EP | 1 323 710 A | | 7/2003 |
|---|---|---|---|
| WO | WO 98/19998 | * | 5/1998 |
| WO | WO 98/19998 A | | 5/1998 |
| WO | WO 01/34594 A | | 5/2001 |
| WO | 01/55105 | | 8/2001 |
| WO | WO 01/96295 A | | 12/2001 |
| WO | WO 03/002553 A | | 1/2003 |
| WO | WO 03/074500 | * | 12/2003 |

OTHER PUBLICATIONS

Kiely, J.S., et al; "Quinolone Antibacterials: Preparation and Activity of Bridged Bicyclic Analogues of the $C_7$-Piperazine"; Journal of Medicinal Chemistry, 1991, vol. 34, No. 2, pp. 656-663.
Mach, R.H., et al; "$^{18}$F-Labeled Benzamides for Studying the Dopamine $D_2$ Receptor with Positron Emission Tomography"; Journal of Medicinal Chemistry, 1993, vol. 36, No. 23, pp. 3707-3720.
Villhauer, E.B., et al; "1-[2-{(5-Cyanopyridin-2-yl)amino]ethylamino}acetyl-2-(S)-pyrrolidine-carbonnitrile: A Potent, Selective, and Orally Bioavailable Dipeptidyl Peptidase IV Inhibitor with Antihyperglycemic Properties"; Journal of Medicinal Chemistry, 2002, vol. 45, No. 12, pp. 2362-2365.
Kitchin, J., et al; Synthesis and Structure-Activity Relationships of a Series of Penicillin-Derived HIV Proteinase Inhibitors: Heterocyclic Ring Systems Containing $P_1$' and $P_2$' Substituents; Journal of Medicinal Chemistry, 1994, vol. 37, No. 22, pp. 3707-3716.
Conti, S., et al; "Chiral Ligands Containing Heteroatoms:13.$^1$ Optically Active 4-(2'-Pyridyl)1,3-oxazolidines: an Improved Synthesis of 2-(2'-Pyridyl)-2-aminoalcohols"; Tetrahedron, 1994, vol. 50, No. 47, pp. 13493-13500.
Mayer, S.C., et al; "Synthesis of New Didemnin B Analogs for Investigations of Structure/Biological Activity Relationships"; Journal of Medicinal Chemistry, 1994, vol. 59, No. 18, pp. 5192-5205.

* cited by examiner

*Primary Examiner*—James O Wilson
*Assistant Examiner*—Erich A Leeser
(74) *Attorney, Agent, or Firm*—Serena Farquharson-Torres

(57) ABSTRACT

Heterocyclic amides useful as inhibitors of dipeptylpeptidase-IV (DPP-IV) enzyme, process for the preparation thereof and intermediates therefore.

13 Claims, No Drawings

COMPOUNDS

Figure 5:
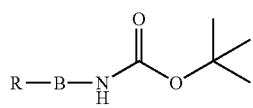

The present invention relates to the novel compounds of the general formula (I) possessing dipeptidyl-peptidase-IV enzyme inhibitory activity, as well as their salts, solvates and isomers, to the pharmaceutical compositions containing them, to the therapeutic application of the compounds of the general formula (I), to the process of preparation of the compounds of the general formula (I) and of the new intermediates of the general formulae (II), (IV), (V), (VII), (VIII) and (IX).

The enzyme, dipeptidyl-peptidase-IV (DPP-IV), which is identical with the lymphocyte surface glycoprotein CD26, a polypeptide with the molecular mass of 110 k Dalton, is formed in the tissues and organs of mammals. This enzyme can be found, among others, in the liver, in the Langerhans islands, in the renal cortex, in the lungs, and in certain tissues of the prostate and small intestine. Significant DPP-IV activity can be observed furthermore in the body liquors (as for instance in the plasma, serum and urine).

DPP-IV is a serine protease type enzyme, which has the unique specificity to cleave dipeptides from the N-terminals of the peptides, where the penultimate amino acid is primarily proline alanine or hydroxy-proline.

DPP-IV enzyme is responsible for the decomposition of the glucagon-like peptides, peptide-1 (GLP-1) and the GIP (gastric inhibitory polypeptide) in the body. The enzyme GLP-1 strongly stimulates the insuline production of the pancrease, thus it has a direct, favourable effect on the glucose homeostasis, therefore DPP-IV inhibitors are suitable for the treatment of non-insulin dependent diabetes mellitus (NIDDM) and other diseases related with the DPP-IV enzyme activity including but not limited to diabetes, obesity, hyperlipidemia, dermatological or mucous membrane disorders, poriasis, intestinal distress, constipation, autoimmune disorders such as enchephalomyelitis, complement mediated disorders such as glomerulonepritis, lipodystrophy, and tissue damage, psychosomatic, depressive, and neurophsychiatric disease such as anxiety, depression, insomnia, schizophrenia, epilepsy, spasm, and chronic pain, HIV infection, allergies, inflammation, arthritis, transplant rejection, high blood pressure, congestive heart failure, tumors, and stress-induced abortions. There are a number of DPP-IV inhibitors known in the literature, but they have disadvantages as regards their activity, toxicity, stability and duration of action.

We have found that the compounds of the general formula (I)

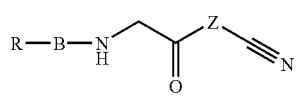
(I)

wherein R stands for:
a nitrogen-containing one- or two-ring aromatic moiety, preferably pyridyl, pyridazinyl, pyrimidinyl, pyrazinyl, imidazolyl, pirazolyl, thiazolyl, isothiazolyl, oxazolyl, isoxazolyl, oxadiazolyl, quinolinyl, isoquinolinyl, cinnolinyl, phthalazinyl, quinazolinyl, quinoxalinyl, benzimidazolyl, indazolyl, benzothiazolyl, benzisothiazolyl, benzoxazolyl or benzisoxazolyl moiety which are optionally mono- or disubstituted independently by one or two of the following groups: C1-4 alkyl groups, C1-4 alkoxy groups, halogen atom, trihalogenomethyl group, methylthio group, nitro group, cyano group, C2-5 alkoxycarbonyl groups or carboxamido group, or p-tolylsulfonyl group; or $R_{1a}$—$CH_2$-group, where the meaning of $R_{1a}$ is hydrogen, C1-4 alkyl group, phenyl, benzyl, phenylethyl, phenylethenyl, naphthyl, pyridyl, quinolyl, isoquinolyl, cinnolinyl, phthalazinyl, quinazolinyl, quinoxalinyl, thienyl, furyl or p-toluenesulfonyl moieties substituted independently by one or more C1-4 alkyl group, C1-4 alkoxy group, alkylenedioxy group, halogen atom, trihalogenomethyl, nitro or cyano group, or $R_{1b}$—CO-group, where the meaning of $R_{1b}$ is C1-4 alkyl group, phenyl, benzyl, phenylethyl, phenylethenyl, naphthyl, pyridyl, quinolyl, isoquinolyl, cinnolinyl, phthalazinyl, quinazolinyl or quinoxalinyl moieties substituted independently by one or more C1-4 alkyl groups, C1-4 alkoxy groups, alkylenedioxy group, halogen atom, trihalogenomethyl, nitro or cyano group; mono- or disubstituted amino group, saturated N-containing heterocyclic moiety, preferably a group containing pyrrolidino, piperidino, piperazino or morpholino ring;

B stands for a group according to the formula (1) or (2) or (3) or (4

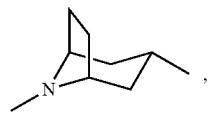
(1)

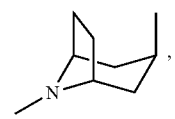
(2)

(3)

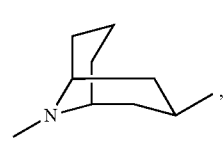
(4)

Z stands for a groups of formula (A) or (B) or (C) or (D) or (E) or (F);

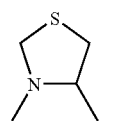
(A)

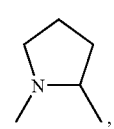
(B)

-continued

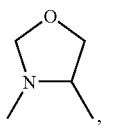, (C)

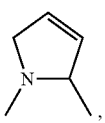, (D)

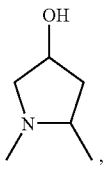, (E)

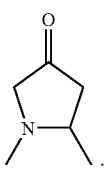. (F)

and the salts, isomers, tautomers, hydrates or solvates of the above compounds possess remarkable advantages in their activity, stability and toxicity.

In accordance with the accepted terminology, the configuration of the carbon atom next to the nitrogen of the N-containing pentacyclic ring is favourably R if Z stands for formula (A) and favourably S if Z stands for formula (B), (C), (D), (E), or (F). Term "halogen atom" means fluorine, chlorine, bromine or iodine atom. Term "C1-4 alkyl group" means methyl, ethyl, propyl, isopropyl, n-butyl, isobutyl or tert.-butyl group. Term "C1-4 alkoxy group" means methoxy, ethoxy, propoxy, isopropoxy, n-butoxy, isobutoxy or tert.-butoxy group. In term "trihalogenomethyl group" halogens mean fluoro, chloro, bromo or iodine. Term "C2-5 alkoxycarbonyl" means methoxycarbonyl, ethoxycarbonyl, propoxycarbonyl, isopropoxycarbonyl, n-butoxycarbonyl, isobutoxycarbonyl or tert.-butoxycarbonyl group. One of the advantageous groups of the general formula (I)—wherein R means pyrimidinyl-, pyridinyl-, pyrazinyl-, pyridazinyl-, benzothiazolyl-, benzisothiazolyl-, benzoxazolyl-, benzisoxazolyl-group which is in a given case independently from each other mono- or disubstituted by one or two of the following group: C1-4 alkyl groups, C1-4 alkoxy groups halogen atom, nitro groups, cyano groups, C2-5 alkoxycarbonyl groups or carboxamido groups, or p-tolylsulfonyl-group; or $R_{1a}$—$CH_2$-group wherein the meaning of $R_{1a}$ is benzyl group or phenylethenyl group substituted in a given case independently by one or more C1-4 alkyl or alkylene dioxy group; or $R_{1b}$ CO-group where the meaning of $R_{1b}$ is phenyl, benzyl, phenylethyl, phenylethenyl or pyperidino group which is in a given case substituted independently from each other by alkylenedioxy group;

B stands for a group of the formula (1) or (2) or (3) or (4);

Z stands for a group of formula (A) or formula (B); —and the salts, isomers, tautomers, hydrates or solvates thereof.

Especially advantageous are the compounds of the general formula (I) wherein the meaning of R is 2-pyrimidyl, 2-pyridazyl or 2-pyridyl group substituted with nitro or cyano group and Z stands for formula (A) or (B); such compounds are for instance (4R)-3-(2-{[8-(2-pyrimidinyl)-8-azabicyclo [3.2.1]oct-3-yl]exo-amino}acetyl)thiazolidine-4-carbonitrile, (4R)-3-(2-{[8-(5-cyano-pyridin-2-yl)-8-azabicyclo [3.2.1]octan-3-yl]-exo-amino}acetyl)thiazolidine-4-carbonitrile, (4R)-3-(2-{[8-(5-cyanopyridin-2-yl)-8-azabicyclo[3.2.1]octan-3-yl]-endo-amino}acetyl) thiazolidine-4-carbonitrile, (4R)-3-(2-{[8-(2-pyrazinyl)-8-azabicyclo[3.2.1]octan-3-yl]-exo-amino}acetyl) thiazolidine-4-carbonitrile and (2S)-1-(2-{[8-(5-nitropyridin-2-yl)-8-azabicyclo[3.2.1]octan-3-yl]-exo-amino}acetyl)pyrrolidine-2-carbonitrile.

The compounds of the general formula (I) according to our invention—wherein the meanings of R and B and Z are as defined above—can be prepared by alkylation of the cyclic primary amines of the general formula (II)

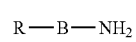

R—B—NH$_2$ (II)

with the chloroacetylcarbonitrile derivatives of the general formula (III)

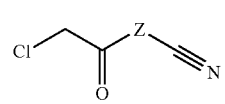

(III)

wherein the meaning of B and Z are as defined above—and, if desired, the resulting compounds are transformed into their salts or solvates (Scheme 1).

In the course of the alkylation the chloroacetylcarbonitrile derivatives of the general formula (III) or cyclic primary amines of the general formula (II) are applied in excess, and the resulting hydrogen chloride is bound by various acid binding agents, preferably by a base, such as for instance 1,8-diazabicyclo[5.4.0]undec-7-ene (DBU), triethylamine, potassium carbonate or polimer-supported 2-terc-butyl-imino-2-diethylamino-1,3-dimethyl-perhydro-1,3,2-diazaphosphorine (PBEMP), which is known as super base. The reaction is preferably performed at a temperature between 25 and 75° C. in 3-16 hours.

The primary amines of the general formula (II) are prepared in a two-step synthesis (Scheme 2). In the first step the starting protected cyclic secondary amine—the compound of the general formula (IV)

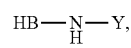

HB—N(H)—Y, (IV)

wherein Y stands tert-butoxycarbonyl group—is arylated with a compound of the general formula (X), wherein X is a halogeno atom in the R—X compounds, preferably chloro or bromo atom. Depending on the meaning of R, arylation can be performed in a polar, protic or aprotic solvent, preferably in an alcohol (ethanol, n-butanol, n-pentanol), at a temperature between 78 and 136° C., or without solvent, in microwave oven, using excess amine or DBU as acid binding agent.

For starting material the protected cyclic secondary amines of the general formula (IV)—known from the literature—are used, tert-butyl 8-azabicyclo[3.2.1]oct-3-yl-exo-carbamate (B=formula (1)) and tert-butyl 8-aza-bicyclo[3.2.1]oct-3-yl-endo-carbamate (B=formula (2)) (*J. Med. Chem.* 1991, 34, 656), or tert-butyl 9-azabicyclo[3.3.1]non-3-yl-exo-carbamate (B=formula (3)) and tert-butyl 9-azabicyclo-[3.3.1]non-3-yl-endo-carbamate (B=formula (4)), (*J. Med. Chem.* 1993, 36, 3707)) (Y=tert-butoxycarbonyl group).

In the second step the protecting Y group is removed by acidic hydrolysis from the arylated amine of the general formula (V)

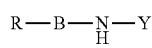
(V)

wherein the meanings of R and Y are as defined above. The reaction is carried out in aqueous hydrochloric acid or in ethanolic hydrogen chloride solution, at a temperature between 25 and 78° C., to produce the cyclic primary amines of the general formula (II) wherein the meaning of R is the same as defined above.

In cases where R is a $R_{1a}$—$CH_2$— or $R_{1b}$—CO-group, the compound of the general formula (IV) is reacted with a compound of general formula (X), namely a $R_{1a}$—$CH_2X$ or $R_{1b}$—COX compound—wherein the meaning of X is a leaving group, preferably a chloro atom—favourably at a temperature around 0° C., using an inorganic or organic base, preferably triethylamine as acid binding agent. From the resulting compound of general formula (V) the protecting group Y—wherein the meaning of Y is tert-butoxycarbonyl group—is cleaved under acidic conditions, preferably by trifluoroacetic acid in dichloromethane solution, at a temperature between 0° C. and 30° C., obtaining thus the compound of the general formula (II)—wherein the meaning of R is a $R_{1a}$—$CH_2$— or $R_{1b}$—CO— group.

The chloroacetylcyano compounds of the general formula (III)—wherein the meaning Z is as defined above—are known (Z=(B): Villhauer et al. *J. Med Chem.* 2002, 45, 2362) or prepared in a four-step synthesis (Scheme 3).

The starting compounds are the N-containing pentacyclic carboxylic acids with the nitrogen protected with tert-butoxycarbonyl group—compounds of the general formula (VI)

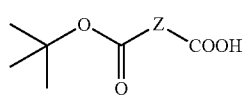
(VI)

wherein the meaning of Z is as defined above. These compounds can be prepared by methods written in the literature (Z=(A): J. Kitcin et al. *J. Med. Chem.* 1994, 37, 3707; Z=(C): S. Conti et al. *Tetrahedron* 1994, 50, 13493; Z=(D): S. C. Mayer et al. *J. Org. Chem.* 1994, 59, 5192)) or commercially available (Z=(E): Aldrich).

In the first step a mixed anhydride is prepared with pivaloyl chloride or chloroformic acid ethyl ester, then the carbamoyl derivatives of the general formula (VII)

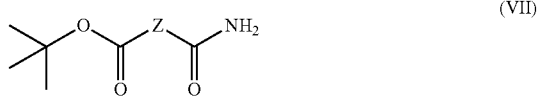
(VII)

wherein the meaning of Z is the same as defined above—are formed with aqueous ammonia. The reaction is preferably carried out in a halogenated solvent (chloroform, dichloromethane) under −5° C. in 2-4 hour reactions.

In the second step the tert-butoxycarbonyl group is cleaved by ethanolic hydrogen chloride solution. Hydrolysis takes place at 0-25° C. in 3-5 hours and the hydrochlorides of the carboxamides of the general formula (VIII)

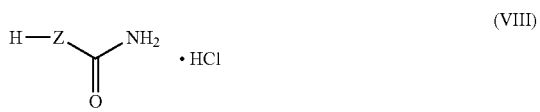
(VIII)

wherein the meaning of Z is the same as defined above—are obtained.

The resulting pentacyclic carboxamides of the general formula (VIII) are in the third step acylated with chloroacetyl chloride, preferably at 0° C. in a halogenated solvent (chloroform, dichloromethane) in 2-4 hours to obtain the chloroacetylcarbamoyl derivatives of the general formula (IX)—wherein the meaning of Z is the same as defined above.

In the fourth step the chloroacetylcarbamoyl derivatives of the general formula (IX)

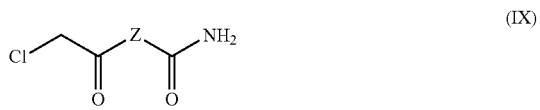
(IX)

wherein the meaning of Z is as defined above—are dehydrated to yield the chloroacetylcarbonitrile derivatives of the general formula (III). Dehydration is preferably carried out with oxalyl chloride in DMF at a temperature below 0° C. or with phosphorous oxychloride in dichloromethane at the boiling point.

Scheme 1

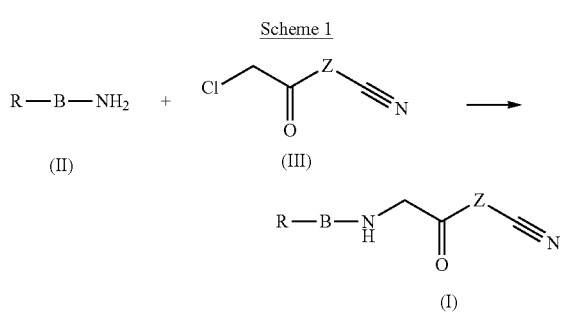

Scheme 2

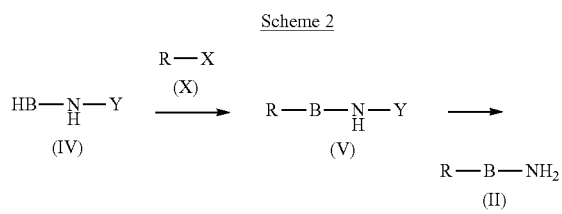

Scheme 3

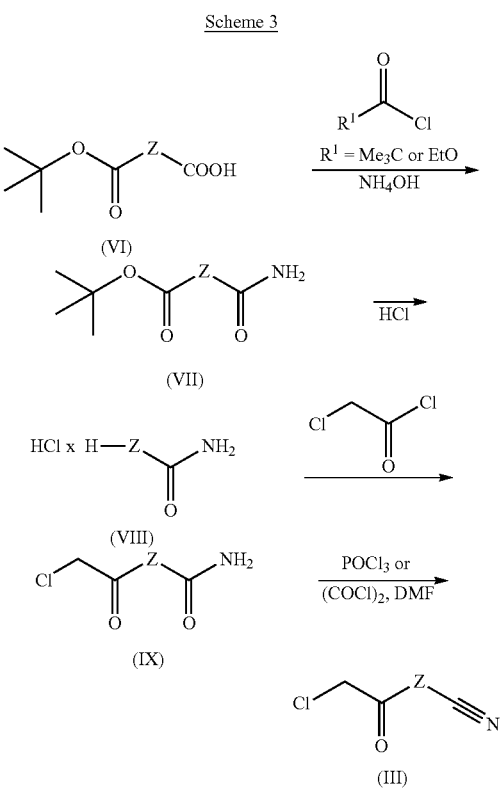

Biological Investigations

DPP-IV enzyme inhibitory activities of the compounds with the general formula (I) were determined by the following method:

Applied Conditions of the Assay:

DPP-IV. source: solubilized crude extractum from CaCo/Tc-7 cells
content: 0.8-1 µg/assay
Substrate: H-Gly-Pro-AMC (Bachem)
Reaction: 1 hour preincubation with inhibitors at 37° C., 30 min reaction time at 37° C.
Stop solution: 1M Na-acetate buffer (pH=4.2)
Reaction mixture: 10 µl enzyme solution
10 µl test compound or assay buffer
55 µl assay buffer
25 µl substrate
300 µl stop solution
Measurement: spectrofluorometric determination by Tecan plate reader
(Ex: 360 nm Em: 465 nm)

The reaction of the DPP-IV enzyme and the H-Gly-Pro-AMC substrate is recorded by the liberation of AMC (7-amino-4-methylcoumarin) at 37° C. in 100 mM Tris-HCl, pH=7.5 (assay buffer). Standard curve of AMC is linear up to 31.25 µM concentration, that is why we used the relative fluorescence unit (RFU) of AMC formed. It is detected using 360 nm excitation and 465 nm emission filters (30 µs integration time, Gain 25, No. of Flashes 50) by Tecan Spectrofluor Plus plate reader. Under these conditions enzyme reaction is linear for at least 30 min, and the enzyme dependence is linear up to 2.5 µg protein (up to 700 RFU). Using 1-0.8 µg of extracted protein $K_m$ for H-Gly-Pro-AMC is 50 µM. Higher than 500 µM substrate concentration caused fluorescent detection problems (inner filter effect) that can be solved by dilution of the samples.

The assay is designed to detect as efficiently as possible the active inhibitors using a 60 min preincubation time at 37° C. The assay is conducted by adding 0.8-1 µg protein extract in 10 µl enzyme solution (using assay buffer: 100 mM Tris-HCl, pH=7.5) to the wells containing the test compounds in 10 µl volume and the 55 µl assay buffer (65 µl assay buffer in the case of controls). After the preincubation period, the reaction is started by the addition of 25 µl 1 mM H-Gly-Pro-AMC substrate solution (250 µM final concentration). The final test volume is 100 µl and the test solution contains 1% DMSO coming from the test compounds solution. Reaction time is 30 min at 37° C., and the reaction is stopped by adding 300 µl 1M Na-acetate buffer, pH=4.2. The fluorescence (RFU) of AMC formed is detected using 360 nm excitation and 465 emission filters in Tecan spectrofluor Plus plate reader (30 µs integration time, Gain 25 No. of Flashes 50).

Inhibition % are calculated using the RFU of control and RFU of blank.

$IC_{50}$ values characteristic for the enzyme inhibitory effect of the compounds of the general formula (I). These compounds show low $IC_{50}$ values in comparison with the known compounds. They are strong and long acting enzyme inhibitors.

The compounds of the general formula (I) and their salts, solvates and isomers can be formulated to orally or parenterally applicable pharmaceutical compositions by methods known per se, by mixing them with one or more pharmaceutically accepted support material or diluent and can be administered as a unitary dosage form.

The appropriate unitary dosage form comprise the oral forms, such as tablets, hard or soft gelatin capsules, powders, granules and oral solutions or suspensions, the sublingual, buccal, intratracheal, intraocular, intranasal forms, by inhalation, the topical, transdermal, sub-cutaneous, intramuscular or intra-venous forms, the rectal forms and the implants. For the topical application, the compounds of the invention may be used as creams, gels, ointments of lotions.

As a example, a unitary dosage form for a compound according to the invention, in the form of a tablet, can comprise the following ingredients:

| | |
|---|---|
| A compound of the general formula (I) | 50.0 mg |
| Mannitol | 223.75 mg |
| Croscarmellose sodium | 6.0 mg |
| Maize starch | 15.0 mg |
| Hydroxypropyl methylcellulose | 2.25 mg |
| Magnesium stearate | 3.0 mg. |

The daily dose of the compounds of the general formula (I) depends on several factors, thus on the nature and seriousness of the disease of the patient, on the mode of application and on the compound itself.

Further details of the invention are demonstrated by the examples below, without limiting the claims to the examples.

EXAMPLE 1

(4R)-3-(2-{[8-(2-Pyrimidinyl)-8-azabicyclo[3.2.1] oct-3-yl]exo-amino}acetyl)thiazolidine-4-carbonitrile The meaning of R is 2-pyrimidinyl group, B means a group of formula (1), Z means a group of formula (A) in general formula (I).

a.) tert-Butyl 8-(2-pyrimidinyl)-8-azabicyclo[3.2.1] oct-3-yl-exo-carbamate

With the General Formula (V)—Where R and B are Given Above, Y is tert-butoxycarbonyl Group 14.7 g (65 mmol) of tert-butyl 8-azabicyclo[3.2.1]oct-3-yl-exo-carbamate (*J. Med. Chem.* 1991, 34, 656) and 8.93 g (78 mmol) of 2-chloropyrimidine and 12.7 ml (85 mmol) of 1,8-diazabicyclo[5.4.0]undec-7-ene were dissolved in 230 ml of n-pentanol and heated under reflux for 4 hours. The solvents were evaporated and the residue was dissolved in 250 ml of chloroform and washed with 2×300 ml of water, dried over sodium sulfate, and purified by column chromatography using n-hexane-ethyl acetate-chloroform (1:1:1) as eluent to result in white crystals which were triturated with n-hexane. Yield: 13.25 g (67%). M.p.: 113-115° C. $^1$H-NMR (CDCl$_3$): δ 1.34 (s, 9H), 1.49 (t, 2H), 1.66-1.97 (m, 6H), 3.89 (br, 1H), 4.61 (d, 2H), 6.60 (t+br, 1+1H), 8.34 (d, 2H).

b.) 8-(2-Pyrimidinyl)-8-azabicyclo[3.2.1]oct-3-yl-exo-amine

With the General Formula (II), where R and B are Given in Step 1a)

13 g (43 mmol) of tert-butyl 8-(2-pyrimidinyl)-8-azabicyclo[3.2.1]oct-3-yl-exo-carbamate was dissolved in a mixture of 120 ml of trifluoroacetic acid and 120 ml of dichloromethane. The solution was stirred for 30 minutes and evaporated. The residue was dissolved in 50 ml of dichloromethane and evaporated. This method was repeated three times and the final organic solution was extracted with 100 ml of saturated aqueous sodium carbonate solution. The layers were separated and the aqueous phase was washed with 4×50 ml of dichloromethane. The combined organic layers were dried over sodium sulfate and evaporated to result in a white powder which was triturated with n-hexane. Yield: 6.7 g (77%). M.p.: 56-59° C. $^1$H-NMR (DMSO-d$_6$): δ 1.29 (t, 2H), 1.64-1.98 (m, 6H), 3.19 (m, 1H), 4.58 (dd, 2H), 6.57 (t, 1H), 8.33 (d, 2H).

c.) tert-Butyl (4R)4-(aminocarbonyl)thiazolidine-3-carboxylate

With the General Formula (VII), where Z Means a Group of Formula (A)

11.1 g (47.6 mmol) of (4R)-3-(tert-butoxycarbonyl)thiazolidine-4-carboxylic acid (*J. Med. Chem.* 1994, 37, 3707) was dissolved in 125 ml of dichloromethane and 8 ml (57.5 mmol) of triethylamine was added. To the resulting mixture 5.85 ml (47.6 mmol) of pivaloyl chloride was added dropwise at −15° C., the mixture was stirred at that temperature for an additional 1 hour, then 12.5 ml of 25% aqueous ammonia was added and stirring was continued for 1 hour. The reaction mixture was washed consecutively with water, 1 N NaOH solution and water, dried over sodium sulfate: 5.9 g (88%) expected product was obtained as colourless oil. $^1$H-NMR (DMSO-d$_6$): □ 1.39 (s, 9H), 3.00 and 3.25 (q, 2×1H), 4.32 and 4.57 (q, 2×1H), 4.3-4.59 (br, 1H), 7.11 and 7.43 (s, 2×1H).

d.) (4R)-Thiazolidine-4-carboxamide hydrochloride

With the General Formula (VIII), where Z Means a Group of Formula (A)

9.25 g (39.8 mmol) of tert-butyl (4R)-4-(aminocarbonyl) thiazolidine-3-carboxylate was dissolved in 45 ml of 25% ethanolic hydrogen chloride solution and stirred for 5 hours. The resulting white crystals were filtered off, washed with diethyl ether. Yield: 5.42 g (81%), mp.: 216-217° C. $^1$H-NMR (DMSO-d$_6$): □ 3.04 and 3.6 (q, 2×1H), 4.8 (q, 2H), 4.8 (q, 1H), 7.6 and 8.17 (s, 2×1H), 10.09 (broad, 2H).

e.) (4R)-3-(2-Chloroacetyl)thiazolidine-4-carboxamide

With the General Formula (IX), where Z Means a Group of Formula (A)

To the suspension of 8.83 g (52.3 mmol) of (4R)-thiazolidine-4-carboxamide hydrochloride in 180 ml of dichloromethane 14.7 ml (105 mmol) of triethylamine, then 4.46 ml (56 mmol) of chloroacetyl chloride in 20 ml of dichloromethane were added dropwise, at 0° C. The mixture was stirred for 30 minutes, allowed to warm to room temperature, stirred for additional 2 hours. The resulting mixture was extracted with 3×200 ml of water, the combined aqueous phase was concentrated in vacuum to ~⅓ of its volume and made alkaline with 20% NaOH solution. The expected product was obtained as white crystals. Yield: 8.12 g (75%), mp.: 119-121° C. $^1$H-NMR (DMSO-d$_6$): □3.05 and 3.23 (q, 2×1H), 4.39-4.54 (m, 3H), 4.71 (d, 2H), 7.20 and 7.43 (s, 2×1H).

f.) (4R)-3-(2-Chloroacetyl)thiazolidine-4-carbonitrile

With the General Formula (III), where Z Means a Group of Formula (A)

7.78 g (37.3 mmol) of (4R)-3-(2-chloroacetyl)thiazolidine-4-carbox-amide was suspended in 65 ml of dry acetonitrile, to the suspension 3.7 ml of dry dimethylformamide, then at −10° C., dropwise, the solution of 3.51 ml (40.6 mmol) of oxalyl chloride in 8 ml acetonitrile was added. The mixture was stirred for 1 hour and 6.6 ml of dry pyridine was dropped to it. After 1 hour of stirring the mixture was evaporated to dryness, the residue was mixed with water and extracted with dichloromethane. The combined organic phase was washed with 1:1 hydrochloric acid, then with water. After drying and evaporation the expected product crystallizes from ethanol: 3.09 g (43%).

Mp: 106-108° C. $^1$H-NMR (CDCl$_3$): □ 3.33 (d, 2H), 4.14 (s, 2H), 4.69 (q, 2H), 5.27 (s, 1H).

g.) (4R)-3-(2-{[8-(2-Pyrimidinyl)-8-azabicyclo[3.2.1]oct-3-yl]exo-amino}acetyl)thiazolidine-4-carbonitrile 245 mg (1.2 mmol) of 8-(2-pyrimidinyl)-8-azabicyclo[3.2.1]oct-3-yl-exo-amine and 191 mg (1 mmol) of (4R)-3-(2-chloroacetyl)thiazolidine-4-carbonitrile and 0.42 ml (3 mmol) of triethylamine were dissolved in 20 ml of dry acetonitrile and stirred at 70° C. for 4 hours and then at room temperature overnight. Then the mixture was evaporated to give a yellow thick oil which was purified by column chromatography using chloroform-methanol (9:1) as the eluent to result in a solid white product which was crystallized from diethyl ether. Yield: 191 mg (53%). M.p.: 135-136° C. $^1$H-NMR (400 MHz, DMSO-$d_6$): δ 1.33 (td, 2H), 1.6-2.0 (m, 5H), 3.05 (tt, 1H), 3.32 (m, 2H), 3.44 (ddd, 2H), 4.63 (s, 2H), 4.56 (d, 1H), 4.61 (m, 2H), 4.70 (m, 1H), 5.23 (dd, 1H), 6.60 (t, 1H), 8.33 (m, 2H).

EXAMPLE 2

(4R)-3-(2-{[8-(5-Cyanopyridin-2-yl)-8-azabicyclo[3.2.1]oct-3-yl]-exo-amino}acetyl)thiazolidine-4-carbonitrile dihydrochloride In the general formula (I) R stands for 5-cyanopyridin-2-yl group, B means for the group of formula (1), Z stands for the group of formula (A).

a.) tert-Butyl 8-(5-cyanopyridin-2-yl)-8-azabicyclo[3.2.1]oct-3-yl-exo-carbamate With General Formula (V), where R and B are Given Above, Y is tert-butoxycarbonyl Group The solution of 415 mg (3 mmol) of 2-chloro-5-cyanopyridine, 679 mg (3 mmol) of tert-butyl 8-azabicyclo[3.2.1]oct-3-yl-exo-carbamate and 0.46 ml (3.1 mmol) of diazabicyclo[5.4.0]undecene in 25 ml of n-pentanol was refluxed for 8 hours. The resulting solution was evaporated in vacuum, the residue was dissolved in dichloromethane, washed with water and dried over sodium sulfate. After purification by chromatography using n-hexane-ethyl acetate-chloroform (2:1:1) as eluent 608 mg (62%) of the title material was obtained. Mp.: 141-143° C. $^1$H-NMR (DMSO-$d_6$): δ 1.38 (s, 9H), 1.44-1.68 (t; 2H), 1.67-2.01 (m, 6H), 3.88 (m, 1H), 4.60 (bs, 2H), 6.61 (d, 1H), 6.80 (d, 1H), 7.81 (dd, 1H), 8.48 (d, 1H).

b.) 8-(5-Cyanopyridin-2-yl)-8-azabicyclo[3.2.1]oct-3-yl-exo-amine

With the General Formula (II)—Where R and B are Given in Step 2a.)

The solution of 657 mg (2 mmol) of tert-butyl 8-(5-cyanopyridin-2-yl)-8-azabicyclo[3.2.1]oct-3-yl-exo-carbamate in 20 ml of 12% ethanolic hydrogen chloride solution was stirred at room temperature for 3 hours. To the resulting white suspension 20 ml of water was added to obtain a solution which was alkalized to pH>10 with 40% potassium hydroxide and extracted with dichloromethane. The organic phase was dried over sodium sulfate and evaporated. The residue was crystallized from n-hexane to obtain 259 mg (57%) of the title compound. Mp.: 123-124° C. $^1$H-NMR (DMSO-$d_6$): δ 1.26 (t, 2H), 1.68-1.93 (m, 6H), 3.12 (m, 1H), 4.57 (b, 2H), 6.78 (d, 1H), 7.79 (dd, 1H), 8.46 (d, 1H).

c.) (4R)-3-(2-{[8-(5-Cyanopyridin-2-yl)-8-azabicyclo[3.2.1]octan-3-yl]-exo-amino}acetyl)thiazolidine-4-carbonitrile dihydrochloride 114 mg (0.6 mmol) of 8-(5-cyanopyridin-2-yl)-8-azabicyclo[3.2.1]oct-3-yl-exo-amine and 114 mg (0.8 mmol) of (4R)-3-(2-chloroacetyl)thiazolidine-4-carbonitrile were dissolved in 20 ml of acetonitrile and to the solution 460 mg (1.1 mmol) of PBEMP is added. The mixture was stirred at 55° C. for 16 hours, scavenger resin was filtered off and the filtrate was evaporated. The residue was purified by chromatography using chloroform-methanol (9:1) eluent. After acidification with ethanolic hydrogen chloride solution and precipitation with diethyl ether the title compound was obtained in the form of white crystals: 75 mg (32%), mp: 204-206° C. $^1$H-NMR (DMSO-$d_6$): δ 1.70-1.78 (m, 4H), 2.01 (m, 4H), 3.37 (m, 2H), 3.67 (m, 1H), 4.07 (m, 1H), 4.21 (m, 1H), 4.56 (d, 1H), 4.76-4.79 (m, 3H), 5.33 (m, 1H), 6.89 (d, 1H), 7.91 (dd, 1H), 8.53 (d, 1H), 9.01 (bs, 2H).

EXAMPLE 3

(4R)-3-(2-{[8-(2-Pyrazinyl)-8-azabicyclo[3.2.1]oct-3-yl]exo-amino}acetyl)thiazolidine-4-carbonitrile dihydrochloride The meaning of R is 2-pyrazinyl group, B means a group of formula (1), Z means a group of formula (A) in general formula (I).

a.) tert-Butyl 8-(2-pyrazinyl)-8-azabicyclo[3.2.1]oct-3-yl-exo-carbamate

With the General Formula (V)—Where R and B are Given Above, Y is tert-butoxycarbonyl Group 0.54 ml (6 mmol) of chloropyrazine, 1.13 g (6 mmol) of tert-butyl 8-azabicyclo[3.2.1]oct-3-yl-exo-carbamate and 0.97 ml (6.5 mmol) of 1,8-diaza-bicyclo[5.4.0]undec-7-ene were dissolved in 40 ml of n-pentanol and heated under reflux for 50 hours. The solvent was evaporated, the residue was dissolved in 50 ml of chloroform, washed with 4×30 ml of water, dried over sodium sulfate, and purified by column chromatography using n-hexane-ethyl acetate-chloroform (3:1:1) as eluent to result in white crystals which was triturated with n-hexane. Yield: 0.55 g (36%). M.p.: 122-123° C. $^1$H-NMR (DMSO-$d_6$): δ 1.34 (s, 9H), 1.44-1.66 (m; 2H), 1.67-1.99 (m, 6H), 3.88 (m, 1H), 4.56 (bs, 2H), 6.59 (d, 1H), 7.77 (d, 1H), 8.07 (dd, 1H), 8.17 (d, 1H).

b.) 8-(2-Pyrazinyl)-8-azabicyclo[3.2.1]oct-3-yl-exo-amine

With General Formula (II), where R and B are Given in Step 3a.)

3.84 g (1.26 mmol) of tert-butyl 8-(2-pyrazinyl)-8-azabicyclo[3.2.1]oct-3-yl-exo-carbamate was dissolved in 20 ml of 12% ethanolic hydrochloric acid and the solution was stirred for 7 hours. Then 20 ml water was added to the formed suspension and the pH was made to 11 with aqueous potassium hydroxide. The layers were separated, the organic phase was dried, evaporated and purified by column chromatography using ethyl acetate-methanol-25% aqueous ammonia solution (17:3:1) as eluent to result in a pale yellow oil. Yield was 167 mg (65%). —H-NMR (DMSO-$d_6$): δ 1.29 (t, 2H), 1.62-1.83 (m, 4H), 1.84-2.00 (m, 2H), 3.12 (s, 1H), 4.57 (dd, 2H), 7.74 (d, 1H), 8.05 (dd, 1H), 8.15 (d, 1H).

c.) (4R)-3-(2-{[8-(2-Pyrazinyl-8-azabicyclo[3.2.1] oct-3-yl]exo-amino}acetyl)thiazolidine-4-carbonitrile dihydrochloride 107 mg (0.52 mmol) of 8-(2-pyrazinyl)-8-azabicyclo [3.2.1]oct-3-yl-exo-amine and 86 mg (0.45 mmol) of (4R)-3-(2-chloroacetyl)thiazolidine-4-carbonitrile were dissolved in 15 ml of acetonitrile and to the solution 0.21 ml (1.5 mmol) of triethylamine was added. The mixture was stirred for 4 hours at 75° C. then evaporated in vacuum. The residue was purified by chromatography using chloroform-methanol (6:1) as eluent. After acidification with ethanolic hydrogen chloride solution and precipitation with diethyl ether, the title compound was obtained in the form of white crystals: 37 mg (19%), mp: 165-170° C. $^1$H-NMR (DMSO-d$_6$): δ 1.76-1.80 (m, 4H), 1.95-2.01 (m, 4H), 3.35 (m, 2H), 3.63 (m, 1H), 4.05 (m, 1H), 4.18 (m, 1H), 4.57 (d, 1H), 4.67 (s, 2H), 4.78 (d, 1H), 5.32 (dd, 1H), 7.87 (d, 1H), 8.15 (dd, 1H), 8.28 (d, 1H), 8.99 (bs, 2H).

EXAMPLE 4

(2S)-1-(2-{[8-(5-Nitropyridin-2-yl)-8-azabicyclo [3.2.1]octan-3-yl]-exo-amino}acetyl)pyrrolidine-2-carbonitrile The meaning of R is 5-nitropyridin-2-yl group, B means a group of formula (1), Z means a group of formula (B) in general formula (I).

a.) tert-Butyl 8-(5-nitropyridin-2-yl)-8-azabicyclo [3.2.1]oct-3-yl-exo-carbamate with (V) general formula, where R and B are given above, Y is tert-butoxycarbonyl group 476 mg (3 mmol) of 2-chloro-5-nitropyridine, 679 mg (3 mmol) of tert-butyl 8-azabicyclo[3.2.1]oct-3-yl-exo-carbamate and 0.46 ml (3.1 mmol) of 1,8-diazabicyclo [5.4.0]undec-7-ene were dissolved in 25 ml of n-pentanol and heated under reflux for 1 hour. The solvent was evaporated, the residue was dissolved in 40 ml of chloroform, washed with 4×40 ml of water, dried over sodium sulfate and evaporated. The solid residue was triturated with diethyl ether to result in yellow crystals. Yield: 731 mg (70%). M.p.: 212-214° C. $^1$H-NMR (DMSO-d$_6$): δ 1.34 (s, 9H), 1.41-1.54 (m; 2H), 1.81-2.16 (m, 6H), 4.00 (m, 1H), 4.75 (bs, 2H), 6.63 (d, 1H), 6.82 (d, 1H), 8.21 (dd, 1H), 8.98 (d, 1H).

b.) 8-(5-Nitropyridin-2-yl)-8-azabicyclo[3.2.1]oct-3-yl-exo-amine

With General Formula (II), where R and B are Given in Step 4a.)

651 mg of tert-butyl 8-(5-nitropyridin-2-yl)-8-azabicyclo [3.2.1]oct-3-yl-exo-carbamate (1.87 mmol) was dissolved in 20 ml of 12% ethanolic hydrochloric acid and the solution was stirred for 3 hours. Under cooling 90 ml 1N sodium hydroxide was added to the formed a suspension which was extracted 4×50 ml dichloromethane. The layers were separated, the organic phase was dried, evaporated and the residue was triturated with n-hexane to result in yellow crystals. Yield is 426 mg (92%). M.p.: 175-178° C. $^1$H-NMR (200 MHz, DMSO-d$_6$): δ 1.29 (t, 2H), 1.68-1.98 (m, 6H), 3.17 (m, 1H), 4.64 (dd, 2H), 6.44 (d, 1H), 8.12 (dd, 1H), 8.95 (d, 1H).

c.) (2S)-1-(2-{[8-(5-Nitropyridin-2-yl]-8-azabicyclo [3.2.1]octan-3-yl-exo-amino}acetyl)pyrrolidine-2-carbonitrile 112 mg (0.45 mmol) of 8-(5-nitropyridin-2-yl)-8-azabicyclo[3.2.1]oct-3-yl-exo-amine was reacted with 103 mg (0.54 mmol) of (2S)-1-(2-chloroacetyl)pyrrolidine-2-carbonitrile (J. Med. Chem. 2002, 45, 2362) in the presence of 450 mg (1.13 mmol) of PBEMP in 20 ml of acetonitrile, as described in Example 2c). After work-up and chromatographic purification (chloroform-methanol 9:1) the product was crystallized from ethyl acetate: 75 mg (41%). Mp.: 177-179° C. $^1$H-NMR (DMSO-d$_6$): δ 1.34 (t, 2H), 1.88 (m, 3H), 1.93-2.01 (m, 6H), 2.11 (m, 2H), 3.07 (m, 1H), 3.32 (m, 1H), 3.38 (m, 1H), 3.55 (m, 1H), 4.50 (b, 1H), 4.71 (m, 1H), 4.92 (b, 1H), 6.81 (d, 1H), 8.20 (dd, 1H), 8.97 (d, 1H).

EXAMPLE 5

(4M-3-(2-{[8-(Pyrimidin-2-yl)-8-azabicyclo[3.2.1] oct-3-yl]exo-amino}acetyl)-1,3-oxazolidine-4-carbonitrile The meaning of R is pyrimidin-2-yl group, B means a group of formula (1), Z means a group of formula (C) in general formula (I).

a.) tert-Butyl (4S-4-(aminocarbonyl)-1,3-oxazolidine-3-carboxylate

With the General Formula (VII), where Z Means a Group of Formula (C)

15.8 g (73 mmol) of (4S)-3-(tert-butoxycarbonyl)-1,3-oxazolidine-4-carboxylic acid (*Tetrahedron*, 1994, 50, 13493) was dissolved in 100 ml of dichloromethane and to the solution 8 ml (73 mmol) of 4-methylmorpholine was added. To the resulting mixture dropwise, at −15° C. 7 ml (73 mmol) of ethyl chloroformate was added and the mixture was stirred at that temperature for 1 hour, then 30 ml of 25% aqueous ammonia solution was added dropwise and the mixture was stirred for 1 hour. The reaction mixture is washed with water, 1 N NaOH solution, then with water, dried over sodium sulphate and evaporated. On addition of diethyl ether 9.10 g (58%) of the above product crystallized. M.p.: 95-96° C. $^1$H-NMR (CDCl$_3$): δ 1.49 (s, 9H), 4.13 (m, 1H), 4.37 (m, 2H), 4.80 (d, 1H), 4.98 (d, 1H). 5.67 (bs, 1H) 6.58 (bs, 1H).

b.) (4S)-1,3-Oxazolidine-4-carboxamide hydrochloride

With the General Formula (VIII), where Z Means a Group of Formula (C)

5.4 g (15.7 mmol) of tert-butyl (4S)-4-(aminocarbonyl)-1, 3-oxazolidine-3-carboxylate was dissolved in 25 ml of 25% ethanolic hydrogen chloride solution and stirred at room temperature for 4 hours. To the resulting suspension 150 ml of diethyl ether was added, the resulting white crystalline material was filtered off. 3.74 g (98%) of the above product are obtained.

M.p.: 155-158° C. $^1$H-NMR (DMSO-d$_6$): δ 4.00 (m, 1H), 4.21-4.39 (m, 2H) 4.68 (d, 1H), 4.77 (d, 1H), 7.82 (s, 1H), 8.17 (s, 1H), 10.12 (br, 2H).

c.) (4M-3-(2-Chloroacetyl)-1,3-oxazolidine-4-carboxamide

With the General Formula (IX), where Z Means a Group of Formula (C)

2.82 g (18 mmol) of (4S)-1,3-oxazolidine-4-carboxamide hydrochloride was suspended in 50 ml of dichloromethane and to the suspension 5.6 ml (40 mmol) of triethylamine was added. To the resulting mixture dropwise, below −10° C. 1.60 ml (20 mmol) of chloroacetyl chloride in 20 ml of dichloromethane was added. After 2 hour of stirring the suspension was poured into 500 ml of ethyl acetate, the precipitated triethylamine hydrochloride was filtered off, the filtrate was evaporated and the residue was crystallized from dichloromethane. 2.30 g (65%) of the above product was obtained in the form of beige crystals. M.p.: 131-133° C. $^1$H-NMR (DMSO-$d_6$): δ 3.91 (m, 1H), 4.06-4.16 (m, 2H), 4.20-4.40 (m, 2H), 5.00 (q, 2H), 7.20 and 7.45 (s, 2×1H).

d.) (4S)-3-(2-Chloroacetyl)-1,3-oxazolidine-4-carbonitrile

With the General Formula (III), where Z Means a Group of Formula (C)

2.12 g (11 mmol) of (4S)-3-(2-Chloroacetyl)-1,3-oxazolidine-4-carboxamide was dissolved in 200 ml of dichloromethane and 20 ml of acetonitrile then 2.62 ml (28 mmol) of phosphorous oxychloride was added thereto. The mixture was heated for 24 hours (if there was remaining starting material then it was refluxed further). During the reflux the solution became red and a sticky solid material was precipitated. The solution is decanted and 50 g of potassium carbonate was added to it. After stirring for an hour the solid salts were filtered off and the solution was evaporated. A red oil was received which was purified with column chromatography (dichloromethane-methanol 9:1). The white crystals were collected and triturated with diethyl ether. Yield: 1.1 g (53%). M.p.: 99-100° C. $^1$H-NMR (CDCl$_3$): δ 3.88-4.10 (m, 2H), 4.10-4.32 (m, 2H), 4.76 (m, 1H), 5.08 (q, 2H).

e.) (4S)-3-(2-{[8-(Pyrimidin-2-yl)-8-azabicyclo[3.2.1]oct-3-yl]exo-amino}acetyl)-1,3-oxazolidine-4-carbonitrile 245 mg (1.2 mmol) of 8-(2-pyrimidinyl)-8-azabicyclo[3.2.1]oct-3-yl-exo-amine and 175 mg (1 mmol) of (4S)-3-(2-Chloroacetyl)-1,3-oxazolidine-4-carbonitrile and 0.42 ml (3 mmol) of triethylamine were dissolved in 20 ml of dry acetonitrile and stirred at 70° C. for 4 hours and then at room temperature overnight. Then the mixture was evaporated to give a yellow thick oil which was purified by column chromatography using dichloromethane-methanol (9:1) as the eluent to result in a solid white product which was crystallized from diethyl ether. Yield: 248 mg (73%). M.p.: 122-125° C. $^1$H-NMR (CDCl$_3$): δ 1.60 (td, 2H), 1.72-1.92 (m, 4H), 2.07 (t, 2H), 3.13 (m, 1H), 3.37 (s, 2H), 3.49 (s, 1H), 3.55 (b, 1H), 4.80 (m, 3H), 5.03 (d, 1H), 6.52 (t, 1H), 8.32 (dd, 2H).

EXAMPLE 6

(2S)-1-(2-{[8-(5-cyanopyridin-2-yl)-8-azabicyclo[3.2.1]oct-3-yl]exo-amino}acetyl)-2,5-dihydro-1H-pyrrole-2-carbonitrile dihydrochloride The meaning of R is 5-cyanopyridin-2-yl group, B means a group of formula (1), Z means a group of formula (D) in general formula (I).

a.) tert-Butyl (2M-2-(aminocarbonyl)-2,5-dihydro-1H-pyrrole-1-carboxy-late

With the General Formula (VII), where Z Means a Group of Formula (D)

To a solution of 4.04 g (18.9 mmol) of (2S)-2,5-dihydro-1H-pyrrole-2-carboxylic acid (*J. Org. Chem.* 1994, 59, 5192) in 60 ml dichloromethane 2.9 ml (21 mmol) triethylamine was added. Pivaloyl chloride (2.4 ml, 20 mmol) in 9 ml dichloromethane was added dropwise at −5° C. and the mixture was stirred at that temperature for 1 hour then 9.5 ml 25% aqueous ammonia solution was added and the mixture was stirred for 4 hours. The reaction mixture was washed with 3×100 ml water. The combined aqueous layer was extracted with 7×50 ml dichloromethane. The combined organic layer was dried over sodium sulphate and evaporated. The oily product was slowly crystallized. 3.09 g (77%) of the above product was obtained. M.p.: 127-133° C. $^1$H-NMR (DMSO-$d_6$): δ 1.36 (s, 9H), 4.07 (m, 2H), 4.70 (m, 1H), 5.70 (m, 1H), 5.95 (m, 1H), 6.99 (br, 1H), 7.38 (br, 1H).

b.) (2S)-2,5-Dihydro-1H-pyrrole-2-carboxamide hydrochloride

With the General Formula (VIII), where Z Means a Group of Formula (D)

6.27 g (29.5 mmol) tert-butyl (2)-2-(aminocarbonyl)-2,5-dihydro-1H-pyrrole-1-carboxylate was dissolved in 170 ml 25% ethanolic hydrogen chloride solution and stirred at room temperature for 6.5 hours. To the resulting suspension diethyl ether (300 ml) was added, the resulting white crystalline material was filtered off. 2.98 g (70%) of the above product was obtained.

M.p.: 181-184° C. $^1$H-NMR (DMSO-$d_6$): δ 4.00 (m, 2H), 4.94 (s, 1H), 5.97 (s, 2H), 7.77 (s, 1H), 8.29 (s, 1H), 8.71 (br, 1H), 10.87 (br, 1H).

c.) (2S)-1-(2-Chloroacetyl)-2,5-dihydro-1H-pyrrole-2-carboxamide

With the General Formula (IX), where Z Means a Group of Formula (D)

To a solution of 0.44 g (3 mmol) (2S)-2,5-dihydro-1H-pyrrole-2-carboxamide hydrochloride in 20 ml dichloromethane 4.1 ml (29.3 mmol) triethylamine was added below −5° C. To this mixture a solution of 0.66 g (6.5 mmol) chloroacetyl chloride in 10 ml dichloromethane was added dropwise. After stirring for 30 min at −5° C. and 3 hours at room temperature the suspension was evaporated. The residue was suspended in 50 ml ethyl acetate, filtered off and washed with ethyl acetate. The filtrate was evaporated and the residue was chromatographed in dichloromethane-methanol (40:1 □ 10:1) as eluent. 0.26 g (46%) of the above product was obtained as colourless oil.

$^1$H-NMR (DMSO-$d_6$): δ 4.32 (m, 2H), 4.37 (q, 2H), 4.85 (m, major) and 5.12 (m, minor)(1H), 5.83 (m, 1H), 6.02 (m, 1H), 7.01 (br, major) and 7.33 (br, minor)(1H), 7.38 (br, major) and 7.69 (br, minor)(1H).

d.) (2S)-1-(2-Chloroacetyl)-2,5-dihydro-1H-pyrrole-2-carbonitrile

With the General Formula (III), where Z Means a Group of Formula (D)

To a solution of 0.25 g (1.32 mmol) (2S)-1-(2-chloroacetyl)-2,5-dihydro-1H-pyrrole-2-carboxamide in 8 ml acetonitrile and 0.15 ml dimethyl-formamide 0.13 ml (1.45 mmol) phosphorous oxychloride in 2 ml acetonitrile was added dropwise at −5° C. The mixture was stirred at room temperature for 4 hours then diluted with 50 ml dichloromethane and washed with water and aqueous sodium hydrogen carbonate, dried and evaporated. The residue was purified by chromatography in dichloromethane-methanol (100:1) as eluent. Yield: 84 mg (37%), colourless oil. $^1$H-NMR (CDCl$_3$): δ 4.08 (s, 2H), 4.48 (m, 2H), 5.40 and 5.60 (m, 1H), 5.86 (m, minor) and 5.92 (m, major)(1H), 6.15 (m, major) and 6.24 (m, minor)(1H).

e.) (2S)-1-(2-{[8-(5-cyanopyridin-2-yl)-8-azabicyclo[3.2.1]oct-3-yl]exo-amino}acetyl)-2,5-dihydro-1H-pyrrole-2-carbonitrile dihydrochloride To a solution of 0.25 g (1.1 mmol) of 8-(5-cyanopyridin-2-yl)-8-azabicyclo[3.2.1]oct-3-yl-exo-amine and 0.16 ml (1.2 mmol) triethylamine in 10 ml acetonitrile 0.17 g (1 mmol) (2S)-1-(2-Chloroacetyl)-2,5-dihydro-1H-pyrrole-2-carbonitrile was added and reaction mixture was stirred at 70° C. for 3 hours. The reaction mixture was evaporated and the residue was dissolved in 50 ml dichloromethane then washed with water, dried and evaporated. The residue was purified by chromatography using CH$_2$Cl$_2$-MeOH (10:1) mixture as eluent. After acidification with ethanolic hydrogen chloride solution and precipitation with diethyl ether, the title compound was obtained in the form of white crystals: 174 mg (39%), mp: 305-9° C. $^1$H-NMR (DMSO-d$_6$): δ 1.76 (m, 4H), 1.99 (m, 4H), 4.05 (t, 2H), 4.39 (m, 2H), 4.71 (br, 1H), 5.56 (m, 1H), 6.00 (m, 1H), 6.28 (m, 1H), 6.90 (d, 1H), 7.92 (dd, 1H), 8.55 (d, 1H), 9.00 (br, 2H).

EXAMPLE 7

(2S,4R)-4-hydroxy-1-(2-{[8-pyrimidin-2-yl)-8-azabicyclo[3.2.1]oct-3-yl]exo-amino}acetyl)pyrrolidine-2-carbonitrile dihydrochloride The meaning of R is pyrimidin-2-yl group, B means a group of formula (1), Z means a group of formula (E) in general formula (I).

a.) tert-butyl (2S,4R)-2-(aminocarbonyl)-4-hydroxy-pyrrolidine-1-carboxylate With the General Formula (VII), where Z Means a Group of Formula (E)

36.32 g (157 mmol) of (2S,4R)-1-(tert-butoxycarbonyl)-4-hydroxy-pyrrolidine-2-carboxylic acid (Aldrich) was dissolved in 450 ml of tetrahydro-furane and to the solution 24 ml (172 mmol) of triethylamine was added. To the resulting mixture, at −10° C. 16.3 ml (172 mmol) of ethyl chloroformate was added dropwise and at the same temperature it was stirred for 1 hour. Keeping the temperature below −5° C., 110 ml of 25% aqueous ammonia solution was added dropwise and the mixture was stirred for 2 hours at room temperature. The reaction mixture was poured into 270 ml of saturated ammonium chloride solution. After separation the aqueous layer was extracted with 2×50 mL of tetrahydrofurane. The combined organic solution was dried over sodium sulphate and evaporated. On addition of diethyl ether 21.19 g (59%) of the above product crystallized. M.p.: 130-132° C. (MH$^+$)=231.

b.) (2S,4R)-1-(2-Chloroacetyl)-4-hydroxypyrrolidine-2-carbonitrile

With the General Formula (III), where Z Means a Group of Formula (E)

(2S,4R)-1-(tert-butoxycarbonyl)4-hydroxypyrrolidine-2-carbonitrile 7.82 g (34 mmol) of tert-butyl (2S,4R)-2-(aminocarbonyl)-4-hydroxypyrrolidine-1-carboxylate was dissolved in 80 ml of pyridine and 12 ml (84 mmol) of trifluoroacetic anhydride was added to the solution dropwise, at −20 C☐. The mixture was stirred at room temperature for a day. The excess of anhydride was hydrolised by addition of some drops of water. To this mixture 200 ml of ethyl acetate was added and it was washed with 10% aqueous hydrogen chloride (to pH 3-5), 50 ml 2 N solution of sodium hydroxide and 50 ml brine. The organic solution was dried over sodium sulphate and evaporated to result in an oil. Yield: 5.35 g (74%). (MH$^{3O}$)=213, (MH$^+$)$_2$=426.

(2S,4R)4-hydroxypyrrolidine-2-carbonitrile-4-methylbenzenesulphonate 6.40 g (30 mmol) of (2S,4R)-1-(tert-butoxycarbonyl)-4-hydroxy-pyrrolidine-2-carbonitrile was dissolved in 100 ml of acetonitrile and 8.56 g (45 mmol) of 4-methylbenzenesulphonic acid monohydrate was added to the solution. The mixture was stirred at room temperature for 24 hours and was evaporated under reduced pressure. 500 ml of diethyl ether was added to the resulting brown oil. It was stirred 10 minutes and kept in the refrigerator for a night. The resulting white crystalline material was filtered off and washed with diethyl ether. 6.31 g (73%) of the above product are obtained. M.p.: 110-113° C.

(2S,4R)-1-(2-Chloroacetyl)-4-hydroxypyrrolidine-2-carbonitrile 6.31 g (22 mmol) of (2S,4R)-4-hydroxypyrrolidine-2-carbonitrile 4-methylbenzenesulphonate was suspended in 37 ml of dichloromethane and 4.1 ml (48 mmol) of triethylamine was added to them. Keeping the temperature of the mixture below −10° C., 2.1 ml (26 mmol) of chloroacetyl chloride in 28 ml of dichloromethane was added dropwise to it. After 2 hours of stirring the suspension was poured into 450 ml of ethyl acetate, the precipitation was filtered off, the filtrate was evaporated and purified by column chromatography using linear gradient of methanol in dichloromethane (0 ☐ 20% v/v) as eluent. 3.51 g (84%) of the above product was obtained in the form of colourless oil. (MH$^+$)=189.

c.) (2S,4R)-4-hydroxy-1-(2-{[8-(pyrimidin-2-yl)-8-azabicyclo[3.2.1]oct-3-yl]exo-amino}acetyl)pyrrolidine-2-carbonitrile 204 mg (1 mmol) of 8-(2-pyrimidinyl)-8-azabicyclo[3.2.1]oct-3-yl-exo-amine, 189 mg (1 mmol) of (2S,4R)-1-(2-chloroacetyl)-4-hydroxypyrrolidine-2-carbonitrile and 0.25 ml (1.8 mmol) of triethylamine were dissolved in 15 ml of dry acetonitrile and stirred at 70° C. for 5 hours and then at room temperature overnight. The acetonitrile was removed under reduced pressure and the residue was dissolved in 15 ml of dichloromethane and 15 ml of brine. After separation the aqueous layer was washed with dichloromethane, and the combined organic solution was dried and evaporated. The formed brown oil was purified by column chromatography using linear gradient of methanol in dichloromethane (0 □ 20% v/v) as eluent. The evaporated product was treated with n-hexane. Yield: 133 mg (38%). M.p.: 165-167° C., (MH$^+$)= 357. $^1$H-NMR (DMSO-d$_6$): δ 1.35 (td, 2H), 1.6-2.0 (m, 7H), 2.20 (dd, 2H), 3.02 (m, 1H), 3.3-3.6 (m, 2H), 3.61 (dd, 1H), 4.35 (dd, 1H), 4.61-4.67 (m, 3H), 5.30 (d, 1H), 6.60 (t, 1H), 8.34 (m, 2H).

EXAMPLE 8

(2S)-4-oxo-1-(2-{[8-(pyrimidin-2-yl)-8-azabicyclo[3.2.1]oct-3-yl]exo-amino}acetyl)pyrrolidine-2-carbonitrile dihydrochloride The meaning of R is pyrimidin-2-yl group, B means a group of formula (1), Z means a group of formula (F) in general formula (I).

357 mg (1 mmol) of (2S,4R)-4-hydroxy-1-(2-{[8-(pyrimidin-2-yl)-8-azabicyclo[3.2.1]oct-3-yl]exo-amino}acetyl)pyrrolidine-2-carbonitrile was dissolved in 20 ml of acetone. At temperature below 0° C. 1.25 ml 8N solution of Jones reagent was added dropwise to the stirred solution. The mixture was stirred for 16 hours at the same temperature. The solution was decanted and the sticky black solid was washed with 2×5 ml of acetone. Saturated potassium carbonate solution was added to the combined acetone solution upto pH 10. The acetone was removed and the residue was extracted with 3×20 ml of ethyl acetate. The combined extracts was washed with 15 ml of brine, dried over sodium sulphate and evaporated. The brown oil was purified by column chromatography using linear gradient of methanol in dichloromethane (0 □ 50% v/v) as eluent. The evaporated product was a yellow oil. Yield: 77 mg (22%). (MH$^+$)=355

Following procedures, outlined for Examples 1-8, the compounds listed in the Table 1 were prepared as a free base or as a salt.

TABLE 1

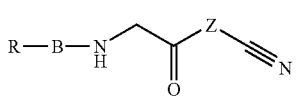

FIG. 1

| Example | R | B (Formula) | Z (Formula) | Melting point, composition physical appearance |
|---|---|---|---|---|
| 9. | 5-nitro-2-methylpyridin-yl (O$_2$N-pyridine) | (1) | (A) | 190-191° C., dihydrochloride, yellow crystals |
| 10. | 5-bromo-2-methylpyridin-yl (Br-pyridine) | (1) | (A) | 156-158° C., yellow crystals |
| 11. | benzoxazol-2-yl | (1) | (A) | 122-123° C., butter-color crystals |
| 12. | benzothiazol-2-yl | (1) | (A) | 262-265° C., dihydrochloride, white crystals |
| 13. | benzyl | (1) | (A) | Aromatic protons: 7.27-7.42(m, 5H), yellow oil |
| 14. | cinnamyl | (1) | (A) | 130-134° C., dihydrochloride, white crystals |

TABLE 1-continued

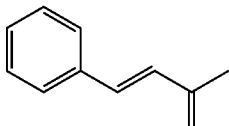

FIG. 1

| Example | R | B (Formula) | Z (Formula) | Melting point, composition physical appearance |
|---|---|---|---|---|
| 15. | 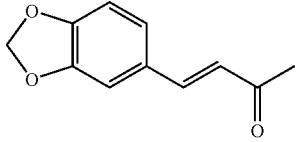 | (1) | (a) | 87-89° C., white crystals |
| 16. | 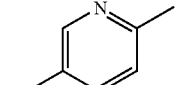 | (1) | (a) | 87-90° C., white crystals |
| 17. | 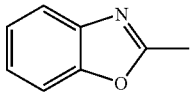 | (2) | (A) | 163-166° C., white crystals |
| 18. | 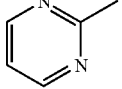 | (3) | (A) | 103-105° C., hydrochloride, white crystals |
| 19. | 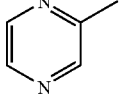 | (4) | (A) | 240-241° C., dihydrochloride, white crystals |
| 20. | 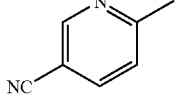 | (1) | (B) | 172-174° C., dihydrochloride, pale yellow crystals |
| 21. | 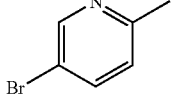 | (1) | (B) | 220-223° C., dihydrochloride, white crystals |
| 22. | 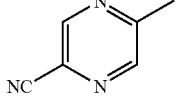 | (1) | (B) | 65-66° C., white crystals |
| 23. | 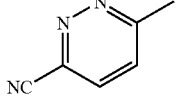 | (1) | (B) | 96-97° C., white crystals |
| 24. | 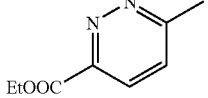 | (1) | (B) | 105-107° C., pale yellow crystals |
| 25. | | (1) | (B) | 164-170° C., hydrochloride, beige crystals |

TABLE 1-continued
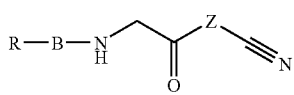
FIG. 1
| Example | R | B (Formula) | Z (Formula) | Melting point, composition physical appearance |
|---|---|---|---|---|
| 26. | 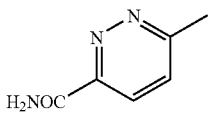 | (1) | (B) | hydrochloride, amorphous beige solid |
| 27. | 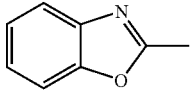 | (1) | (B) | 333-335° C., dihydrochloride, white crystals |
| 28. | 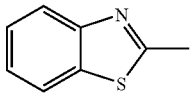 | (1) | (B) | 266-269° C., dihydrochloride, white crystals |
| 29. | 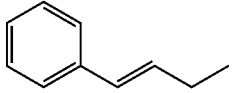 | (1) | (B) | 88-90° C., white crystals |
| 30. | 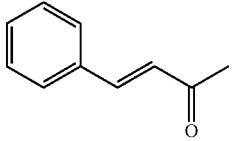 | (1) | (B) | 60-63° C., white crystals |
| 31. | 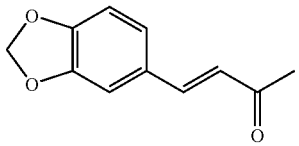 | (1) | (B) | 83-86° C., white crystals |
| 33. | 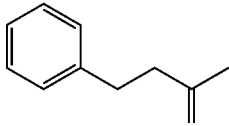 | (1) | (B) | 77-80° C., dihydrochloride, white crystals |
| 33. | 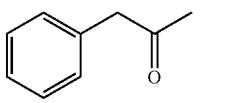 | (1) | (B) | 151-153° C., white crystals |

TABLE 1-continued $$R-B-\underset{H}{N}-CH_2-\underset{O}{C}(=O)-Z-C\equiv N \quad (I)$$

FIG. 1

| Example | R | B (Formula) | Z (Formula) | Melting point, composition physical appearance |
|---|---|---|---|---|
| 34. | 4-(methylsulfonyl)phenyl | (1) | (B) | 46-49° C., white crystals |
| 35. | phenacyl (PhC(O)CH₂–) | (1) | (B) | 65-67° C., white crystals |
| 36. | 4-MeO-phenacyl | (1) | (B) | 52-55° C., white crystals |
| 37. | 4-O₂N-phenacyl | (1) | (B) | 86-89° C., white crystals |
| 38. | 2-naphthacyl | (1) | (B) | 70-75° C., white crystals |
| 39. | piperidin-1-yl-carbonylmethyl | (1) | (B) | 102-104° C., white crystals |
| 40. | (6-methyl-5-cyano)pyridin-3-yl | (2) | (B) | 141-143° C., white crystals |
| 41. | (2,6-dimethyl-3-cyano)pyridinyl | (1) | (C) | 174-176° C., white crystals, dihydrochloride |

Following procedures outlined for Examples 1a), 2a), 3a) and 4a) the compounds V listed in the Table 2 were prepared.

TABLE 2
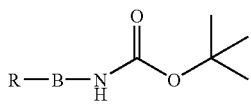
(V)
FIG. 5
| Example | R | B (Formula) | Characterisation (M.p., LC/MS or aromatic protonss by $^1$H-NMR [DMSO-d$_6$] |
|---|---|---|---|
| 2.1. | 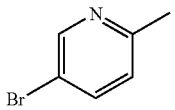 | (1) | 6.75(d, 1H), 7.60(d, 1H), 8.12(s, 1H) |
| 2.2. | 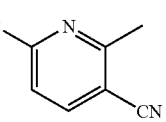 | (1) | 2.37(s, 3H), 6.65(d 1H), 7.84(d, 1H) |
| 2.3. | 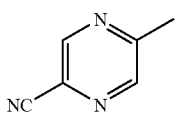 | (1) | [MH]$^+$ = 330 |
| 2.4. | 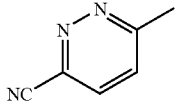 | (1) | 227-230° C. |
| 2.5. | 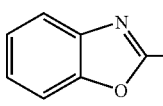 | (1) | 163-165° C. |
| 2.6. | 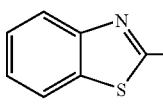 | (1) | 7.16(t, 1H), 7.35(t, 1H), 7.53(d, 1H), 7.86 (d, 1H) |
| 2.7. | 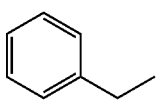 | (1) | 177-179° C. |
| 2.8. | 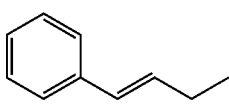 | (1) | 127-130° C. |
| 2.9. | 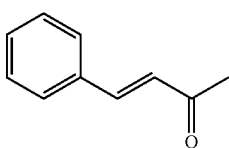 | (1) | 153-156° C. |
| 2.10. | 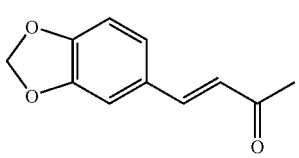 | (1) | 166-169° C. |

TABLE 2-continued (V)

| Example | R | B (Formula) | Characterisation (M.p., LC/MS or aromatic protonss by $^1$H-NMR [DMSO-d$_6$] |
|---|---|---|---|
| 2.11. | phenyl-CH$_2$CH$_2$-C(O)-CH$_3$ | (1) | 153-155° C. |
| 2.12. | phenyl-CH$_2$-C(O)-CH$_3$ | (1) | 139-141° C. |
| 2.13. | 4-methylphenyl-S(O)$_2$- | (1) | 195-198° C. |
| 2.14. | phenyl-C(O)- | (1) | 143-145° C. |
| 2.15. | 4-MeO-phenyl-C(O)- | (1) | 125-128° C. |
| 2.16. | 4-O$_2$N-phenyl-C(O)- | (1) | 143-146° C. |
| 2.17. | 2-naphthyl-C(O)- | (1) | 92-96° C. |
| 2.18. | piperidinyl-C(O)- | (1) | 149-151° C. |
| 2.19. | 5-cyano-2-methylpyridinyl | (2) | 154-156° C. |

TABLE 2-continued $$R-B-\underset{H}{N}-\overset{O}{C}-O-C(CH_3)_3 \quad (V)$$

FIG. 5

| Example | R | B (Formula) | Characterisation (M.p., LC/MS or aromatic protonss by $^1$H-NMR [DMSO-d$_6$] |
|---|---|---|---|
| 2.20. | benzoxazol-2-yl | (3) | 6.99(t, 1H), 7.13(t, 1H), 7.26(d, 1H), 7.36 (d, 1H) |
| 2.21. | pyrimidin-2-yl | (4) | 6.50(t, 1H), 8.33(m, 2H) |

Following procedures outlined for Examples 1b), 2b), 3b) and 4b) the compounds II listed in the Table 3 were prepared.

TABLE 3

$$R-B-NH_2 \quad (II)$$

FIG. 2

| Example | R | B (Formula) | Characterisation (M.p. or aromatic protons by $^1$H-NMR [DMSO-d$_6$]) |
|---|---|---|---|
| 3.1. | 5-bromo-2-methylpyridin-3-yl | (1) | 6.40(d, 1H), 7.60(d, 1H), 8.14(s, 1H) |
| 3.2. | 6-methyl-2-methyl-3-cyanopyridin-yl | (1) | 2.35(s, 3H), 6.62(d, 1H), 7.81(d, 1H) |
| 3.3. | 5-cyanopyrazin-2-yl | (1) | 115-117° C. |
| 3.4. | 6-cyanopyridazin-3-yl | (1) | 120-123° C. |
| 3.5. | benzoxazol-2-yl | (1) | 127-129° C. |
| 3.6. | benzothiazol-2-yl | (1) | 126-127° C. |
| 3.7. | phenylethyl | (1) | 7.20-7.35(m, 1H) |

TABLE 3-continued

R—B—NH$_2$ (II)
FIG. 2

| Example | R | B (Formula) | Characterisation (M.p. or aromatic protons by $^1$H-NMR [DMSO-d$_6$]) |
|---|---|---|---|
| 3.8. | (phenyl-CH=CH-CH$_2$-CH$_3$) | (1) | 109-112° C. |
| 3.9. | (phenyl-CH=CH-C(O)-CH$_3$) | (1) | 107-109° C. |
| 3.10. | (methylenedioxyphenyl-CH=CH-C(O)-CH$_3$) | (1) | 90-93° C. |
| 3.11. | (phenyl-CH$_2$-CH$_2$-C(O)-CH$_3$) | (1) | 7.16-7.33(m, 1H) |
| 3.12. | (phenyl-CH$_2$-C(O)-CH$_3$) | (1) | 88-90° C. |
| 3.13. | (4-methylphenyl-SO$_2$-) | (1) | 107-109° C. |
| 3.14. | (phenyl-C(O)-CH$_3$) | (1) | 73-75° C. |
| 3.15. | (4-MeO-phenyl-C(O)-CH$_3$) | (1) | 7.43(dd, 2H), 6.87(dd, 2H), 3.93(s, 3H) |
| 3.16. | (4-O$_2$N-phenyl-C(O)-CH$_3$) | (1) | 97-100° C. |
| 3.17. | (naphthyl-C(O)-CH$_3$) | (1) | [M]$^+$ = 280 |

TABLE 3-continued

R—B—NH$_2$ (II)
FIG. 2

| Example | R | B (Formula) | Characterisation (M.p. or aromatic protons by $^1$H-NMR [DMSO-d$_6$]) |
|---|---|---|---|
| 3.18. | 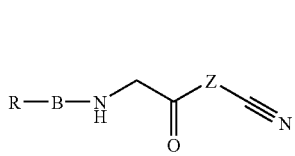 | (1) | [M]$^+$ = 237 |
| 3.19. | 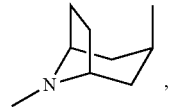 | (2) | 6.49(d, 1H), 7.76(dd, 1H), 8.43(d, 1H) |
| 3.20. | 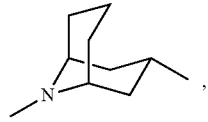 | (3) | 7.00(t, 1H), 7.14(t, 1H), 7.26(d, 1H), 7.37 (d, 1H) |
| 3.21. | 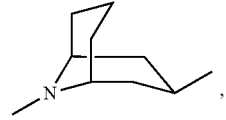 | (4) | 6.50(t, 1H), 8.29(d, 1H), 8.31(d, 1H) |

The invention claimed is:

1. A compound of formula (I)

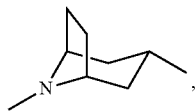 (I)

wherein

R is pyridyl, optionally mono- or disubstituted independently by $C_{1-4}$ alkyl, $C_{1-4}$ alkoxy, halogen, trihalogenomethyl, methylthio, nitro, cyano, $C_{2-5}$ alkoxycarbonyl or carboxamido;

$R_{1a}$—CH$_2$ where $R_{1a}$ is pyridyl, optionally independently substituted with one or more $C_{1-4}$ alkyl, $C_{1-4}$ alkoxy, alkylenedioxy, halogen, trihalogenomethyl, nitro or cyano; or $R_{1b}$—CO, where $R_{1b}$ pyridyl, optionally independently substituted with one or more $C_{1-4}$ alkyl, $C_{1-4}$ alkoxy, alkylenedioxy, halogen, trihalogenomethyl, nitro or cyano; or $R_{1b}$ is piperidino;

B is a group of formula (1), (2), (3), or (4)

(1)

-continued

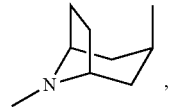 (2)

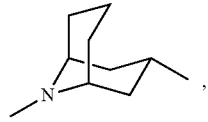 (3)

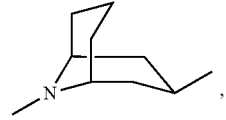 (4)

and

Z is a group of formula (A), (B), (C), (D), (E), or (F);

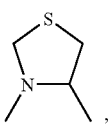 (A)

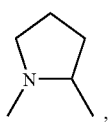 (B)

-continued

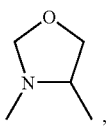
(C)

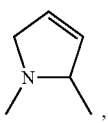
(D)

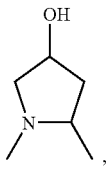
(E)

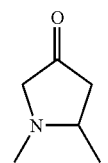
(F)

or a salt or hydrate thereof.

2. The compound according to claim 1 wherein
R is pyridyl, optionally independently mono- or disubstituted with $C_{1-4}$ alkyl, $C_{1-4}$ alkoxy, halogen, trihalogenomethyl, methylthio, nitro, or cyano;
$R_{1a}$—$CH_2$, where $R_{1a}$ is pyridyl, optionally independently substituted with one or more $C_{1-4}$ alkyl, $C_{1-4}$ alkoxy, alkylenedioxy, halogen, trihalogenomethyl, nitro or cyano; or
$R_{1b}$—CO where $R_{1b}$ is pyridyl, optionally independently substituted with one or more $C_{1-4}$ alkyl, $C_{1-4}$ alkoxy, alkylenedioxy, halogen, trihalogenomethyl, nitro or cyano; or
$R_{1b}$ is piperidino;
or a salt or hydrate thereof.

3. The compound according to claim 1 wherein
R is pyridyl, optionally independently mono- or disubstituted with $C_{1-4}$ alkyl, $C_{1-4}$ alkoxy, halogen, nitro, cyano, $C_{2-5}$ alkoxycarbonyl or carboxamido; or
$R_{1b}$CO where $R_{1b}$ is piperidino; and
Z is a group of formula (A) or formula (B);
or a salt or hydrate thereof.

4. The compound according to claim 3 wherein
R is pyridyl, optionally independently mono- or disubstituted with $C_{1-4}$ alkyl, $C_{1-4}$ alkoxy, halogen, nitro, or cyano;
or
$R_{1b}$CO where $R_{1b}$ is piperidino;
or a salt or hydrate thereof.

5. The compound according to claim 4 wherein R is pyridyl, substituted with nitro or cyano, and B is a group of formula (1) or (2); or a salt or hydrate thereof.

6. A compound selected from the group consisting of:
(4R)-3-(2-{[8-(5-Cyanopyridin-2-yl)-8-azabicyclo[3.2.1]octan-3-yl]-exo-amino}acetyl)thiazolidine-4-carbonitrile;
(4R)-3-(2-{[8-(5-Cyanopyridin-2-yl)-8-azabicyclo[3.2.1]octan-3-yl]-endo-amino}acetyl)thiazolidine-4-carbonitrile; and
(2S)-1-(2-{[8-(5-Nitropyridin-2-yl)-8-azabicyclo[3.2.1]octan-3-yl]-exo-amino}acetyl)pyrrolidine-2-carbonitrile;
or a salt, or hydrate thereof.

7. A pharmaceutical composition comprising a compound according to claim 1 or a pharmaceutically acceptable salt or hydrate thereof, together with a pharmaceutically acceptable support material or diluent.

8. A pharmaceutical composition comprising a compound according to claim 2 or a pharmaceutically acceptable salt or hydrate thereof, together with a pharmaceutically acceptable support material or diluent.

9. A pharmaceutical composition comprising a compound according to claim 3 or a pharmaceutically acceptable salt or hydrate thereof, together with a pharmaceutically acceptable support material or diluent.

10. A pharmaceutical composition comprising a compound according to claim 4 or a pharmaceutically acceptable salt or hydrate thereof, together with a pharmaceutically acceptable support material or diluent.

11. A pharmaceutical composition comprising a compound according to claim 5 or a pharmaceutically acceptable salt or hydrate thereof, together with a pharmaceutically acceptable support material or diluent.

12. A pharmaceutical composition comprising a compound according to claim 6 or a pharmaceutically acceptable salt, or hydrate thereof, together with a pharmaceutically acceptable support material or diluent.

13. A process for preparing the compound according to claim 1 comprising reacting a compound of formula (II)

$$R\text{—}B\text{—}NH_2 \quad (II)$$

with a compound of formula (III)

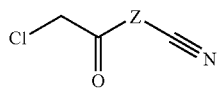
(III)

wherein in the above formulas R, B, and Z are as defined in claim 1.

* * * * *